US00PP24136P2

(12) United States Plant Patent
Kwon et al.

(10) Patent No.: US PP24,136 P2
(45) Date of Patent: Jan. 7, 2014

(54) APPLE TREE NAMED 'PICNIC'

(50) Latin Name: ***Malus domestica* Borkh.**
Varietal Denomination: Picnic

(75) Inventors: Soon-Il Kwon, Gyeongbuk (KR); Mok-Jong Kim, Gyeongbuk (KR); Png-Nyol Paek, Gyeongbuk (KR); Jong-Chul Nam, Gyeongbuk (KR)

(73) Assignee: The Rural Development Administration, Republic of Korea, Gyeonggi-Do (KR)

( * ) Notice: Subject to any disclaimer, the term of this patent is extended or adjusted under 35 U.S.C. 154(b) by 31 days.

(21) Appl. No.: 13/374,387

(22) Filed: Dec. 27, 2011

(51) Int. Cl.
*A01H 5/00* (2006.01)

(52) U.S. Cl.
USPC ..... Plt./161

(58) Field of Classification Search
USPC ..... Plt./161
See application file for complete search history.

(56) References Cited

U.S. PATENT DOCUMENTS

PP6,519 P 1/1989 Yoshida et al.
PP7,001 P 8/1989 Hiraragi

OTHER PUBLICATIONS

Pluto Plant Variety Database 2012-06. Search for Picnic.*
Daesung, C. et al., Effects of Modified Atmosphere Film Packaging Application and Controlled Atmosphere Storage on Changes of Quality Characteristics in 'Hongro' and 'Gamhong' Apples, Korean Journal of Horticultural Science & Technology, 2006, pp. 48-55, vol. 24, No. 1.
"Korea Seed & Variety Service, Searching Plant Variety Protection Database: Apple Malus Domestica Borkh", Retrieved from web on Nov. 30, 2012, <http://www.seed.go.kr/english/function/system_05_view.jsp?appl_idty=596>, p. 1.

* cited by examiner

*Primary Examiner* — Annette Para
(74) *Attorney, Agent, or Firm* — MacMillan, Sobanski & Todd, LLC

(57) ABSTRACT

A new and distinct variety of apple tree variety 'Picnic' is described herein. 'Picnic' fruit is small, conical, red, not smooth, low brightness, and matures in late September.

8 Drawing Sheets

STATEMENT REGARDING U.S. FEDERAL FUNDING

Research related to this invention was not made with any United States Government support and the United States Government has no rights in the invention.

Genus and species: *Malus domestica* Borkh.

Variety denomination: 'Picnic'.

BACKGROUND OF THE INVENTION

I. Field & Utility Summary

The present invention relates to a new and distinct variety of apple tree. The apple tree is particularly useful in that it can be propagated clonally and provides distinctive fruit attributes.

II. Cultivation Summary

'Picnic' originated from a planned cross in 1994 in Korea. The seed parent was 'Fuji' and the pollen parent was 'Sansa'.

III. Parental Comparisons

'Picnic' is similar to parent 'Fuji' in fruit color. 'Picnic' differs from parent 'Fuji' in fruit size, shape and timing of maturation. 'Picnic' fruit is small, conical, and matures in late September, whereas parent 'Fuji' fruit is medium to large, oblate, and matures in late October.

'Picnic' is similar to parent 'Sansa' in fruit size and shape. 'Picnic' differs from parent 'Sansa' in fruit color and maturation. 'Picnic' fruit surface is red and matures in late September, whereas 'Sansa' fruit surface is striped or mottled red over lighter color and matures in late August.

'Picnic' is different from both parents 'Sansa' and 'Fuji' because 'Picnic' fruit is small, conical, red, and matures in late September.

IV. Closest Non-Parental Comparator

'Picnic' differs from non-parent comparator 'Gamhong' in fruit shape, size, smoothness, and brightness. 'Picnic' fruit is conical, small, not smooth, and has low brightness, whereas 'Gamhong' fruit is oblong, large, smooth, and has medium brightness.

V. Breeding History

In 1994, pollen from 'Sansa' apple tree was applied to emasculated flowers of a 'Fuji' apple tree in Korea. Between 2001 and 2003, the seeds derived from this pollination were extracted from mature fruit derived from this cross and screened to obtain favorable seedlings. Between 2004 and 2008, the seeds were screened and regional adaptability tests were carried out before a variety was selected and named 'Picnic' in 2008. The selected variety was then planted by asexual propagation for five generations.

VI. Asexual Reproduction

Asexual reproduction of 'Picnic' has been achieved using traditional grafting techniques. Five centimeter sections of branches from a stable 'Picnic' plant were cut, and grafted onto pieces of rootstock. Approximately three buds were present on each 5 cm branch piece. The grafted plant was grown under standard conditions.

VII. Stability

Observations of trees from clonal propagations indicate that all trees have proven true to type and identical in all appearances to the original tree. No genetic variations were found, and therefore, its traits are stable.

SUMMARY OF THE INVENTION

'Picnic' apple tree produces fruit that is small, conical, red, not smooth, low brightness, and matures in late September.

DETAILED BOTANICAL DESCRIPTION

Figure 1:
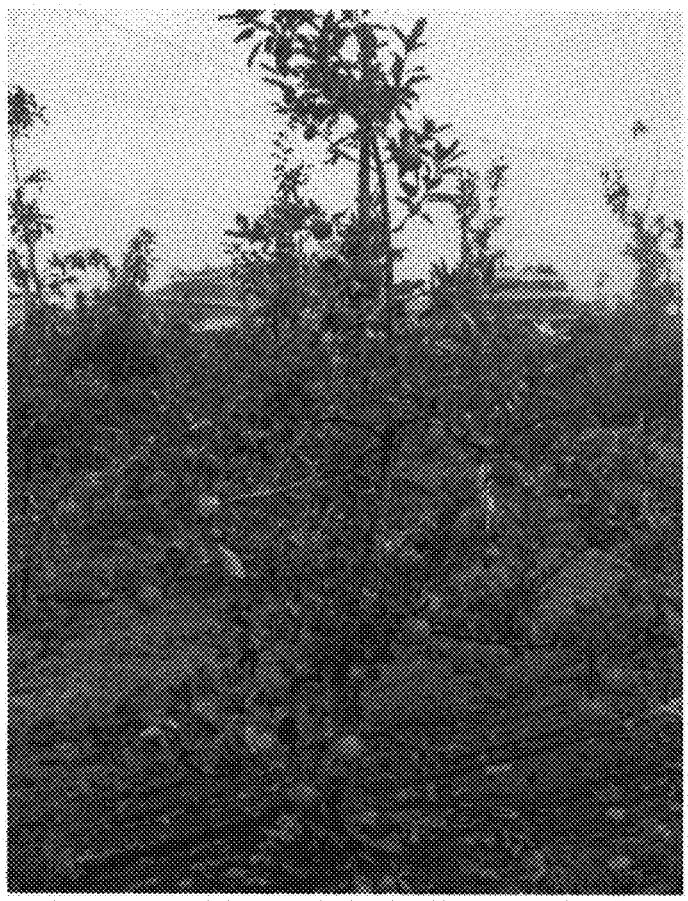
FIG. 1 shows the live 'Picnic' plant.
Figure 2:
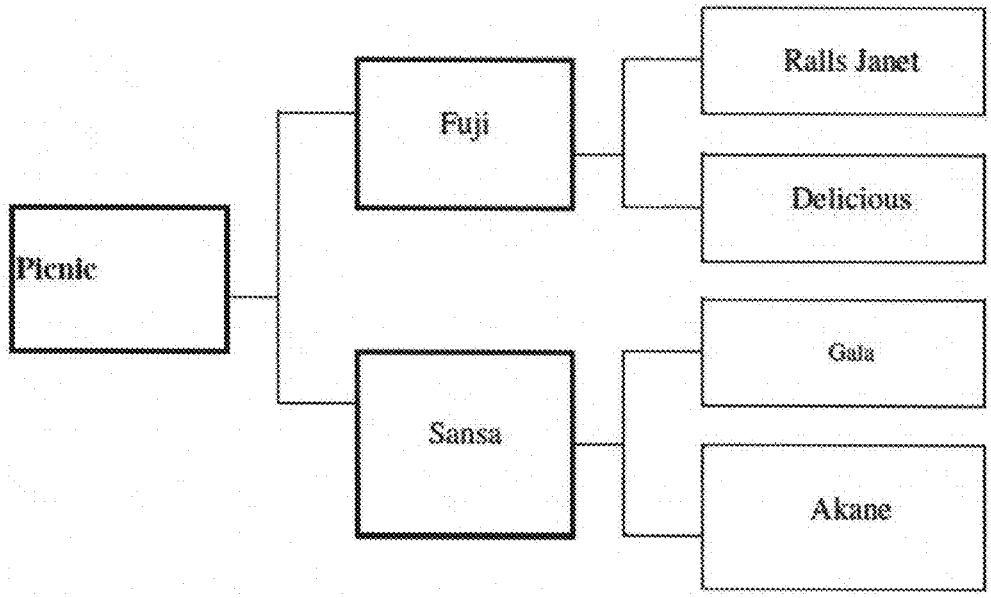
FIG. 2 is a schematic depicting the parentage of 'Picnic'.
Figure 3:
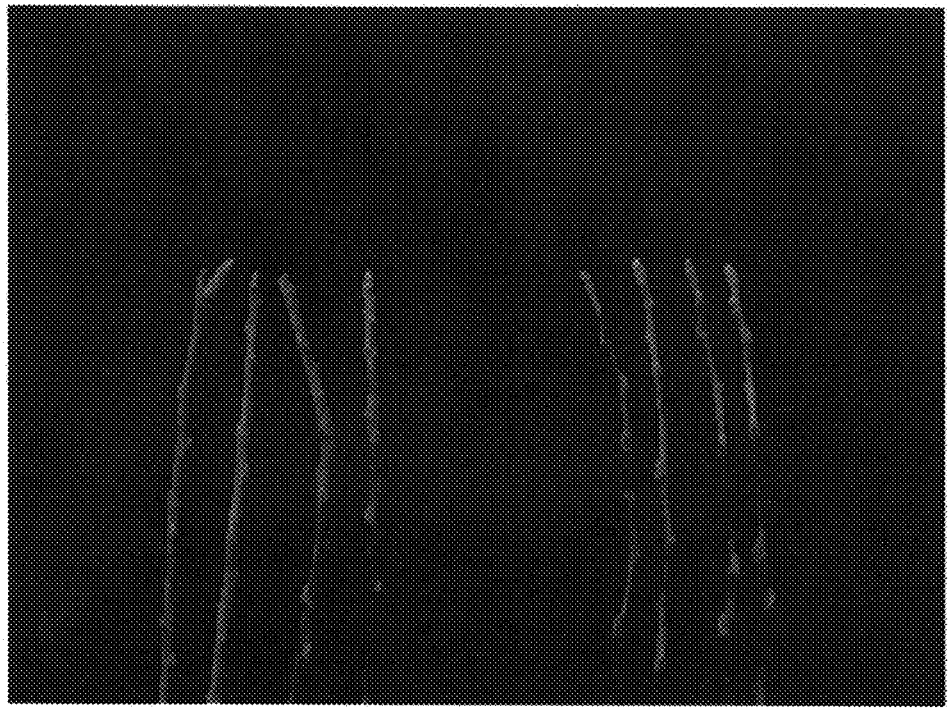
FIG. 3 shows dormant wood of 'Picnic'.
Figure 4:
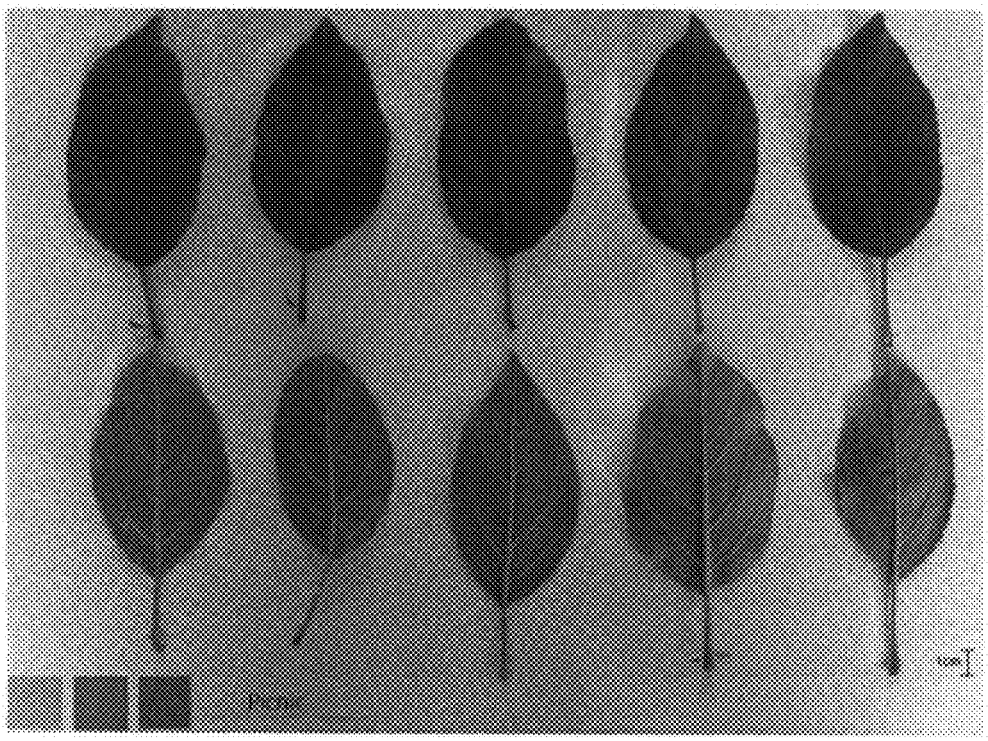
FIG. 4 shows the adaxial (upper) and abaxial (lower) surface of mature leaves of 'Picnic'.
Figure 5:
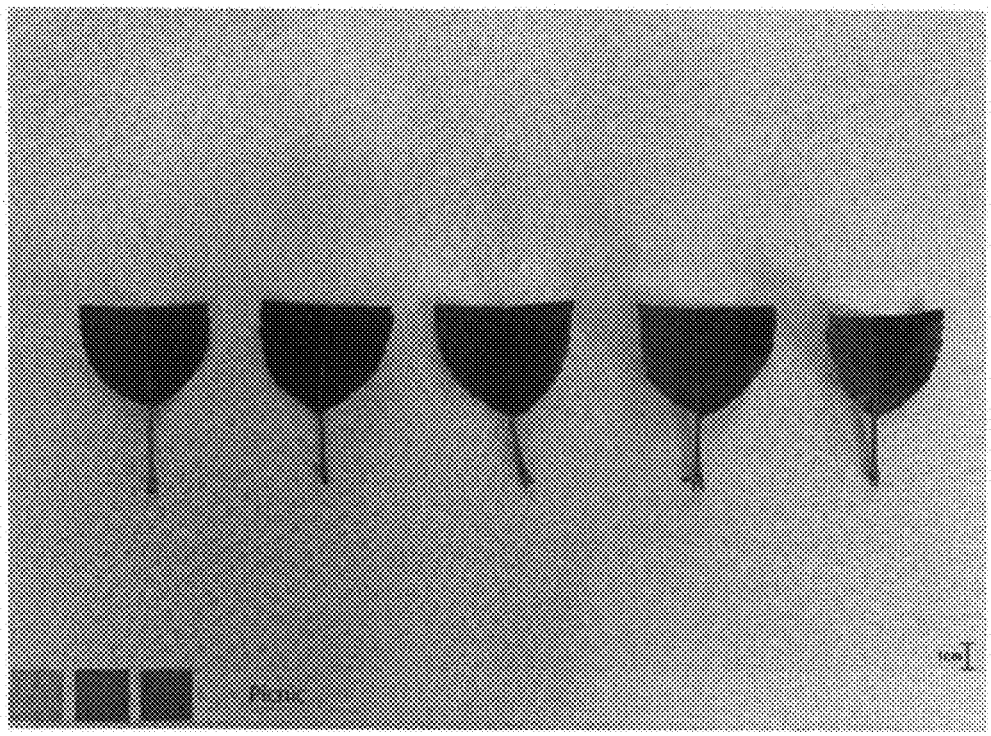
FIG. 5 shows the adaxial (upper) cut surface of leaves of 'Picnic'.
Figure 6:
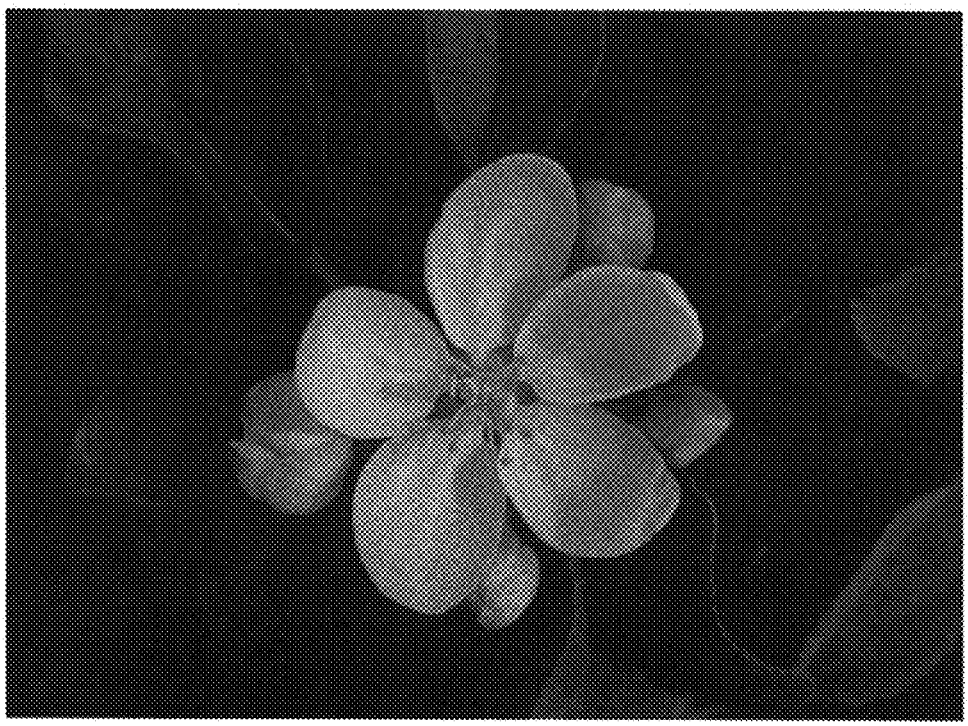
FIG. 6 shows typical inflorescence of 'Picnic'.
Figure 7:
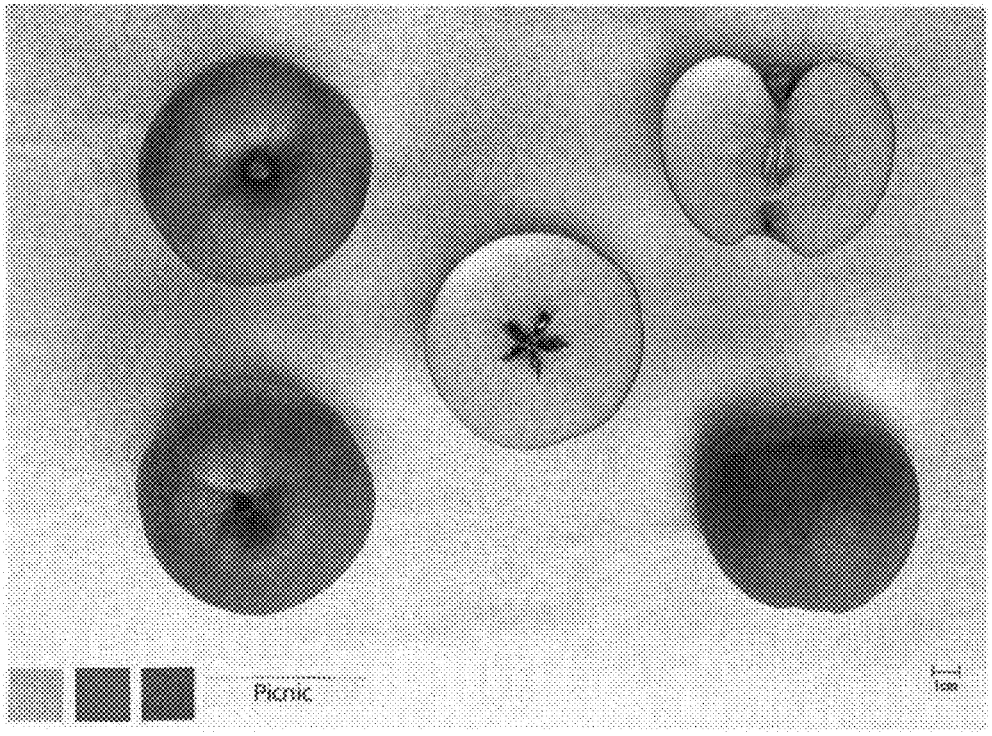
FIG. 7 shows various aspects of the fruit of 'Picnic', including a view of the cavity (stem end), basin (calyx end), side view, a transverse sectional and a longitudinal sectional, showing the seeds, flesh and outer skin.
Figure 8:
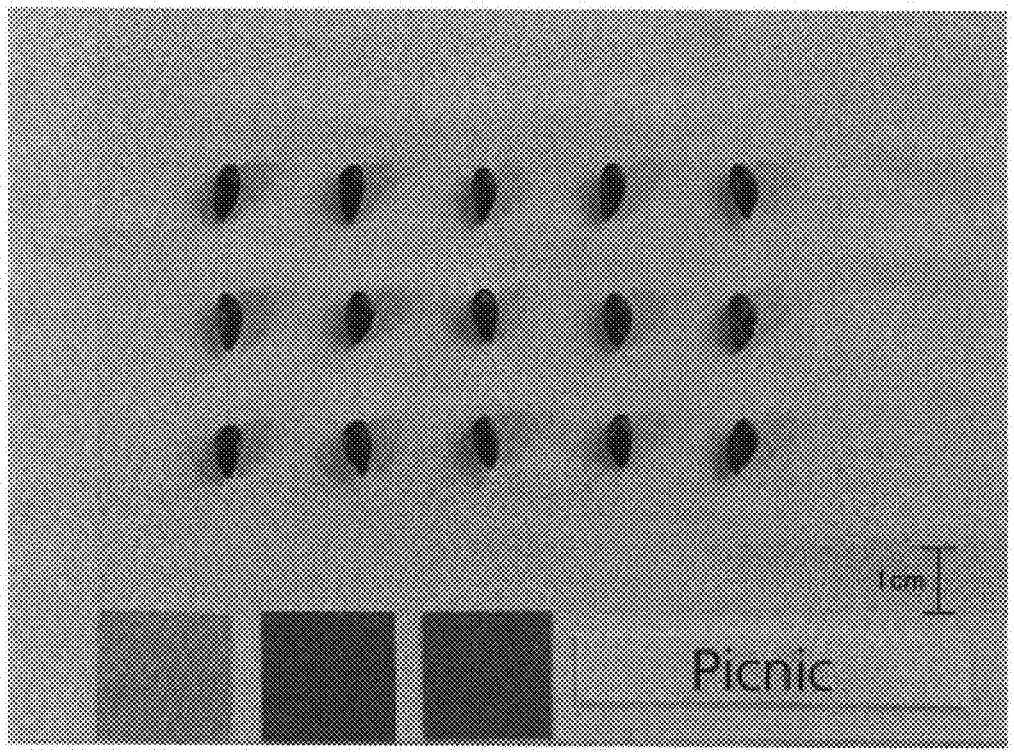
FIG. 8 shows seeds of 'Picnic'.

The following description of 'Picnic' contains references to color names taken from The Royal Horticultural Society Colour Chart (R.H.S.), 2001 edition. Botanical descriptions follow the Manual of Cultivated Plants (Bailey, 1949).

Tree:

*Habit*.—Upright-semi-spreading. 6 year old under good growing conditions.

*Size*.—Height: 4.5 m. Width: 2 m.

Trunk: 1 year old branches of dormant wood.

*Diameter of the middle*.—5.07 mm.

*Length*.—1.86 mm.

*Number of lenticels*.—Middle.

Stem:

*Color* (*RHS*).—166A.

*Length*.—45 cm.

*Diameter*.—6.2 mm.

*Pubescence*.—Many.

*Shape*.—Straight.

*Odor*.—None (of bruised stem).

*Internode length*.—2.48 cm.

Leaves:

*Mature leaves*.—Leaf arrangement: Dislocated. Shape: Length of leaf is longer than width.

*Size*.—Length: 8.72 cm. Width: 4.60 cm.

*Apex*.—Sharp.

*Base*.—Narrow.

*Margin*.—Jagged.

*Upper surface*.—Color (RHS): 141A. Texture: Rough.

*Lower surface*.—Color (RHS): 134A. Texture: Rough.

*Venation*.—There are five on each side, and arranged asymmetric.

*Pubescence*.—Medium.

*Lobes* (*absent*).—Number: Zero.

*Petiole*.—Length: 31.55 mm. Shape: Straight. Color (RHS): 59A. Pubescence: Medium. Diameter: 1.6 mm.

Flowers:

*Inflorescence*.—Number of individual flowers per stem: 5.

*Individual flower*.—Axillary, terminal: Rare. Symmetry: Asymmetry.

*Petals*.—Size (L×W): Diameter 40 mm. Shape: Oval. Apex (RHS): 155D. Base (RHS): 155D. Margin (RHS): 155D. Color at peak of bloom: Upper (RHS): 155D. Center (RHS): 62A.

*Pedicels*.—Color (RHS): 177D. Pubescence: Medium. Length: 25.3 mm.

*Sepals*.—Number: 5. Size (L×W): 7 mm×7 mm. Shape: Triangle. Pubescence: Medium. Color (RHS): 155D.

*Stamens*.—Number: 18. Size (L×W): L 18 mm. Color (RHS): 3A. Pollen color (RHS): 3A. Pubescence: Rare.

*Pistils*.—Number: 5. Size of style (L×W): L 20 mm. Color of style (RHS): 4D. Color of stigma (RHS): 4D.

*Bracts*.—Number: 18. Size (L×W): L18 mm×W12 mm. Color (RHS): 134A. Shape:

Fruit:

*Size*.—Height: 66.5 mm. Diameter: 76.3 mm.

*Shape*.—Color (RHS).—45A.

*Observed fruit weight*.—233 g.

*Flesh*.—High firmness.

*Sepal*.—7 mm×7 mm.

*Calyx*.—Size: 7 mm×7 mm.

*Flesh*.—Color (RHS): 3D. Taste: Good.

*Aperture eye stalk bloom*.—

*Percent soluble solids*.—14.2° Bx.

*Titratable acidity*.—0.43%.

*Penetrometer*.—43.15N.

Seed:

*Color* (*RHS*).—200D.

*Size*.—Height: 9 mm. Diameter: 4 mm.

*Number*.—8.

Disease resistance: Resistance to bitter rot.

The invention claimed is:

1. A new and distinct variety of apple tree named 'Picnic' as described and illustrated herein.

* * * * *